(12) United States Patent  
Ogawa (10) Patent No.: US 6,244,710 B1
(45) Date of Patent: *Jun. 12, 2001

(54) OPHTHALMOGICAL PHOTOGRAPHING APPARATUS

(75) Inventor: Tetsuji Ogawa, Utsunomiya (JP)

(73) Assignee: Canon Kabushiki Kaisha, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 15 days.

(21) Appl. No.: 09/467,013

(22) Filed: Dec. 20, 1999

(30) Foreign Application Priority Data

Dec. 30, 1998 (JP) .................................................. 10-377632
Nov. 12, 1999 (JP) .................................................. 11-322077

(51) Int. Cl.⁷ ....................................................... A61B 3/14
(52) U.S. Cl. ............................................................. 351/206
(58) Field of Search ..................................... 351/205, 206, 351/207, 208, 210; 396/51, 226

(56) References Cited

U.S. PATENT DOCUMENTS 5,459,536 * 10/1995 Shalon et al. .......................... 351/226
5,706,071 * 1/1998 Tokunaga .............................. 351/206

FOREIGN PATENT DOCUMENTS 0 772 342   5/1997 (EP).

* cited by examiner

Primary Examiner—George Manuel
(74) Attorney, Agent, or Firm—Fitzpatrick, Cella, Harper & Scinto (57) ABSTRACT

A photographing switch is pressed to start a photographing operation. All detected image information is input as digital data into an image memory. An image processing section detects the highest and lowest luminance values with respect to a set area. An ophthalmogical photographing apparatus sets a signal compression ratio of digital signals based on these highest and lowest luminance values so that a high-gradation image which is primarily required for diagnostic purposes is obtained.

27 Claims, 8 Drawing Sheets

OPHTHALMOGICAL PHOTOGRAPHING APPARATUS

BACKGROUND OF THE INVENTION

1. Field of the Invention

The present invention relates to an ophthalmogical photographing apparatus having an image-capturing device for taking photographic images of an eye to be examined.

2. Description of the Related Art

There is known an ophthalmogical photographing apparatus which obtains an image of an examined eye as an electronic image by an image-capturing device, etc., instead of by conventional silver-halide film.

However, in the above-described conventional example, when an image of an examined eye is input as an electronic image, photographic tolerance (latitude) for a conventional silver-halide film is narrow. Therefore, for example, when an image of the eyegrounds is to be input, it is very difficult to obtain information efficiently from a papilla of the optic nerve (optic disk) having high luminance which contains much information and from the retina having low luminance, in particular, the macula lutea. Furthermore, the reflectance of the eyegrounds differs greatly from person to person, and when a photograph is taken using an inappropriate amount of light with respect to this reflectance, an inefficient image having a small area containing useful information with respect to a predetermined dynamic range is formed.

When a photograph of an image of an examined eye is taken, there are cases in which white flaring occurs at the peripheral portion of the image due to the degree of curvature of the cornea and photographic error. In this case, since information of the high-luminance portion, which is unnecessary for the predetermined dynamic range, is assigned closely, an inefficient image is formed. In a similar manner, a black aperture portion in the peripheral portion of the image is a factor which produces an inefficient image in which unnecessary information is assigned to a low-luminance portion.

Furthermore, in electronic images in general, when the amount of image data is large, a greater storage capacity is required, and processes, such as a replay, are thereafter slow. Some ophthalmogical photographing apparatuses use a technique for taking photographs continuously at very short intervals. However, in this case, a problem arises in that the processing speed per image must be shortened greatly.

SUMMARY OF THE INVENTION

An object of the present invention is to provide an ophthalmogical photographing apparatus in which a decrease in image quality is minimized with respect to a primarily target area in the image of an eye being examined while reducing the image processing time.

To achieve the above-mentioned object, according to a first aspect of the present invention, there is provided an ophthalmogical photographing apparatus including: an image-capturing device, having a plurality of pixels, for converting an image of an examined eye into electrical signals; a digital conversion section for converting the output of the plurality of pixels into digital signals; first and second detection units for detecting a high-level signal and a low-level signal, respectively, of the level signals indicating luminance levels of the digital signals in predetermined area pixels of the image-capturing device; and a setting unit for setting a signal compression ratio of the digital signals of the digital conversion section on the basis of the high-level signal and the low-level signal.

The setting unit may set the compression ratio of level signals by the digital conversion section which is present between the high-level signal and the low-level signal to differ from the compression ratio of level signals by the digital conversion section which is not present between the high-level signal and the low-level signal.

Furthermore, the setting unit may set the compression ratio of level signals, by the digital conversion section which is present between the high-level signal and the low-level signal, to be smaller than the compression ratio of level signals by the digital conversion section which is not present between the high-level signal and the low-level signal.

A predetermined pixel area for detecting the high-level signal preferably contains the papilla of the examined eye, and a predetermined pixel area for detecting the low-level signal preferably contains the macula lutea of the examined eye.

A fixed-viewing target for guiding the fixed-viewing position of an examined eye is preferably provided, and the predetermined pixel area is changed in accordance with the fixed-viewing target.

According to a second aspect of the present invention, there is provided an ophthalmogical photographing apparatus including: an image-capturing unit for converting an examined eye image into electrical signals; a fixed-viewing target for directing the attention of the examined eye for fixed-viewing; an area setting unit for setting an image-capturing area of the image-capturing unit in accordance with the position of the fixed-viewing target; a luminance detection unit for detecting the luminance of the examined eye image information obtained from the image-capturing unit with respect to the area set by the area setting unit; and an image processing unit for performing signal processing on image information of the image-capturing unit in accordance with an output of the luminance detection unit.

According to a third aspect of the present invention, there is provided an ophthalmogical photographing apparatus including: an image-capturing unit for converting an examined eye image into electrical signals; an eye information generation unit for generating information for indicating whether an examined eye is the right eye or the left eye; a luminance detection unit for detecting luminance information with respect to a predetermined area of the image-capturing unit in accordance with an output of the eye information generation unit; and an image processing unit for performing signal processing on examined eye image information by the image-capturing unit in accordance with an output of the luminance detection unit.

In the accompanying drawings, illustrative embodiments of the invention are shown from which these and other objects, novel features, and advantages will be readily apparent.

DESCRIPTION OF THE PREFERRED EMBODIMENTS

The present invention will now be described in detail with reference to the embodiments shown in the figures.

Figure 1:
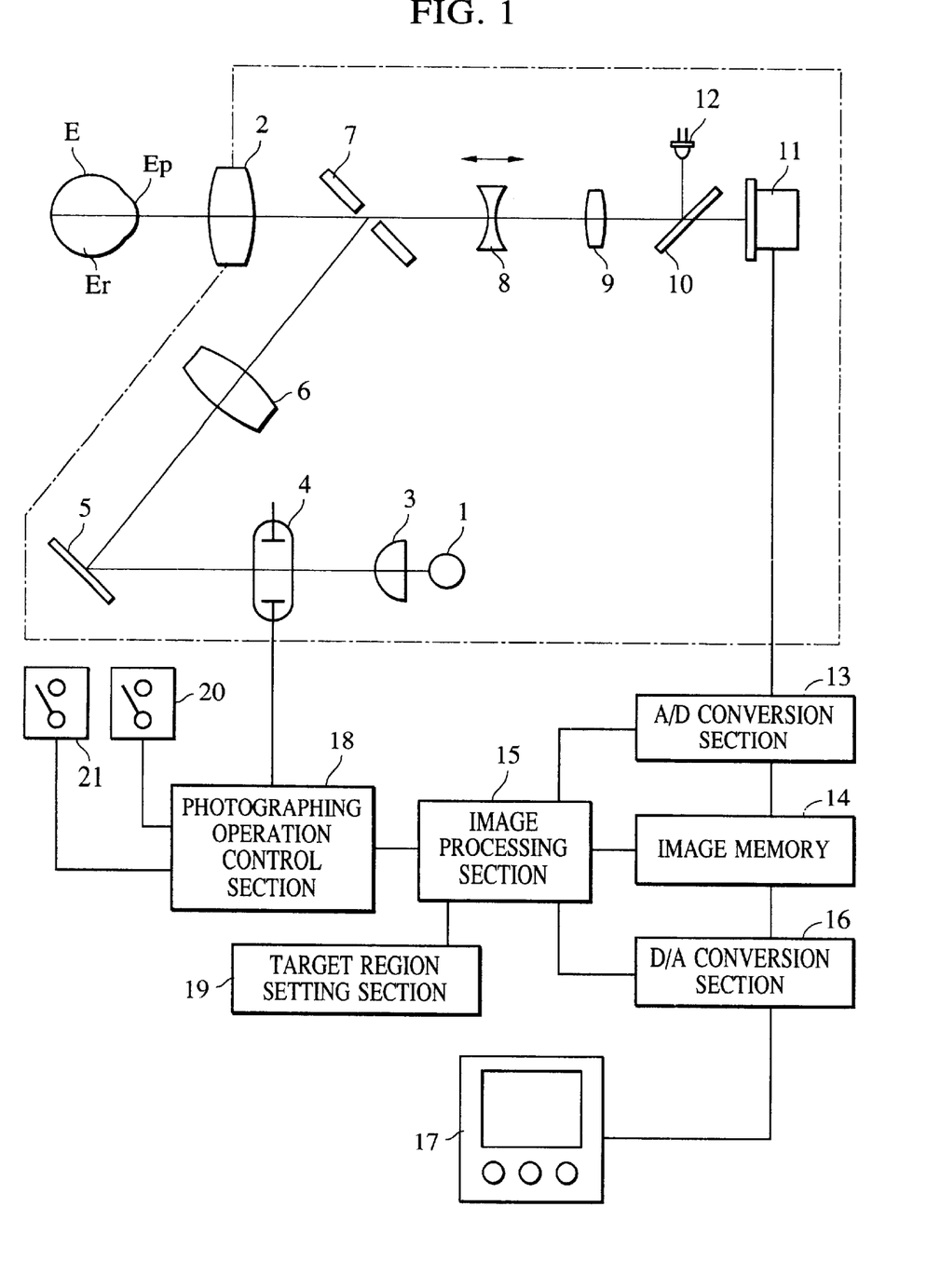
FIG. 1 shows the construction of a first embodiment of the present invention.

FIG. 1 shows the construction of a fundus camera according to a first embodiment of the present invention. Arranged in sequence along the light path from a light source (infrared light source) 1 for observation to an objective lens 2 facing an examined eye E, are a capacitor lens 3, a light source (visible light source) 4 for photography, a mirror 5, a relay lens 6, and a mirror 7 with a hole. Along the light path rearward of the mirror 7 with a hole, a focusing lens 8, a photographic lens 9, a half-mirror 10, and photographing means 11 are arranged, with a fixed-viewing target 12 being placed in an incident direction of the half-mirror 10. The image-capturing device and the eyegrounds are placed so as to be conjugated with each other.

Reference numeral 11 denotes image-capturing means for color photography, in which a pixel sequence is placed in a two-dimensional manner. Outputs of all the pixels of the image-capturing means 11 are converted into digital signals (level signals) for each pixel by an A/D (analog/digital) conversion section 13 having, for example, 10-bit resolution. The A/D conversion section 13 is connected to an image memory 14 and an image processing section 15. The outputs of the image memory 14 and the image processing section 15 are connected to a monitor 17 via a D/A (digital/analog) conversion section 16. The output of the image processing section 15 is connected to a photographing operation control section 18 and a target region setting section 19. An output of a photographing switch 20 is connected to the photographing operation control section 18, and an output of the photographing operation control section 18 is connected to the light source 4 for photography. Reference numeral 21 denotes a detection switch for determining whether the target eyegrounds is of the right eye or the left eye.

A near-infrared light beam which is emitted from the light source 1 for observation passes through the capacitor lens 3, the mirror 5, and the relay lens 6, is reflected in the peripheral portion of the mirror 7 with a hole, passes through the objective lens 2, the pupil Ep of the examined eye E, and illuminates the eyegrounds Er. The illuminated eyegrounds image passes through the pupil Ep, the objective lens 2, the hole of the mirror 7 through the focusing lens 8, the photographic lens 9, and the half-mirror 10, and is formed into an image on the image-capturing means 11. It is possible for the examinee to see the fixed-viewing target 12 by the light reflected by the half-mirror 10 along the light path, causing the line of sight to be guided, and the position of the examined eye E is thereby fixed.

The image formed on the image-capturing means 11 is displayed on the monitor 17 continuously via the A/D conversion section 13, the image memory 14, and the D/A conversion section 16. An operator performs position alignment while viewing this image and photographs the eyegrounds. When performing position alignment, monochromatic observation by near-infrared light is performed.

When the photographing switch 20 is pressed when position alignment is completed, this is detected by the photographing operation control section 18, and the light source 4 for photography emits light of predetermined luminous energy. This photographing light passes through the light path in a manner similar to that for the observation light after exiting the mirror 5, and an eyegrounds image of the examined eye E is formed on the image-capturing means 11. The obtained video signal (RGB signal) is converted by the A/D conversion section 13 into digital information, for example, at 10-bit resolution for each pixel and is temporarily stored in the image memory 14, and the image processing section 15 begins image processing.

Figure 2:
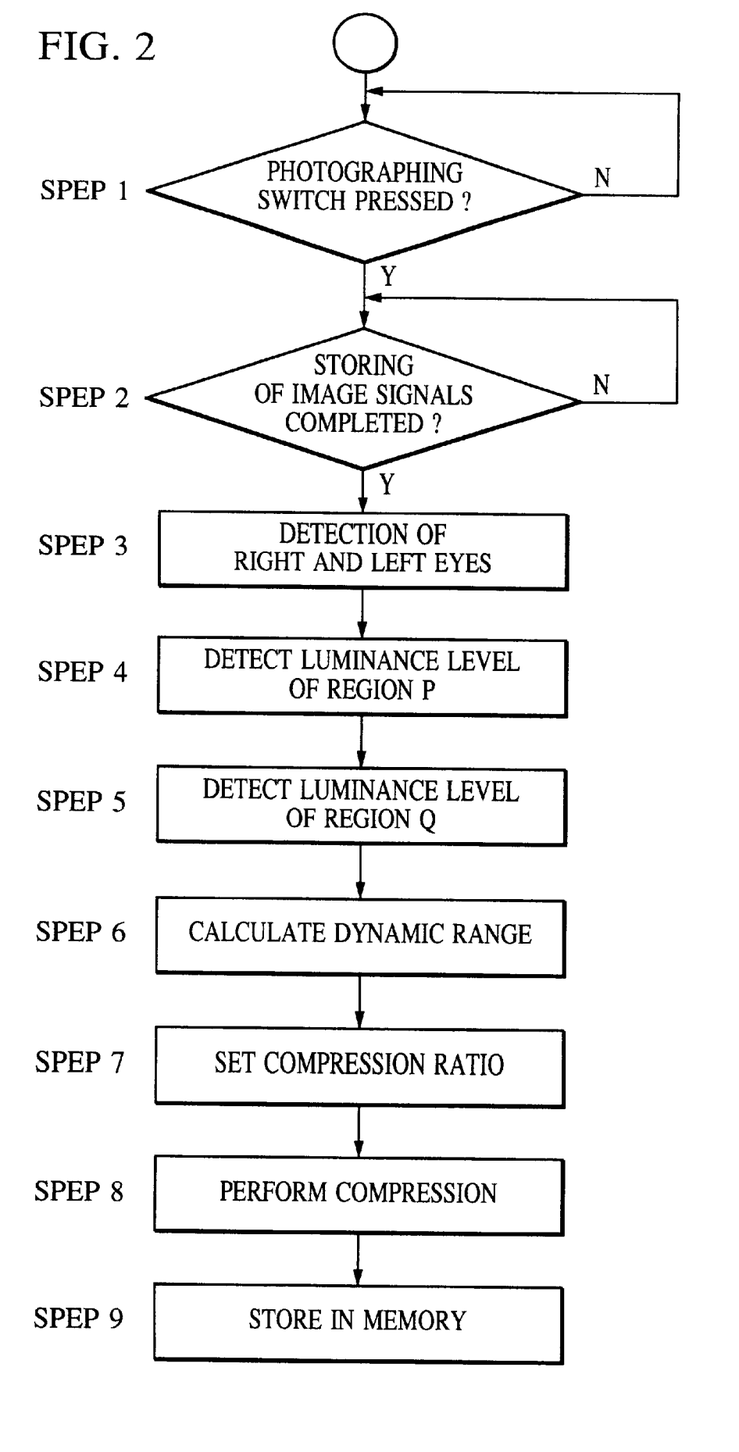
FIG. 2 is a flowchart of image processing.

FIG. 2 is a flowchart of image processing. As a result of the photographing switch 20 being pressed, initially, a photographing operation is started (step 1). All the pixel signals which are stored after detecting the starting are converted into digital data at 10-bit resolution, and all the image information is input to the image memory 14 (step 2). Next, a right-left eye detection means 21 detects the position of the optical system with respect to the examined eye E in order to determine whether it is the right eye or the left eye (step 3). Based on an output of this right-left eye detection means 21, luminance information with respect to the predetermined target area is detected.

Figure 3:
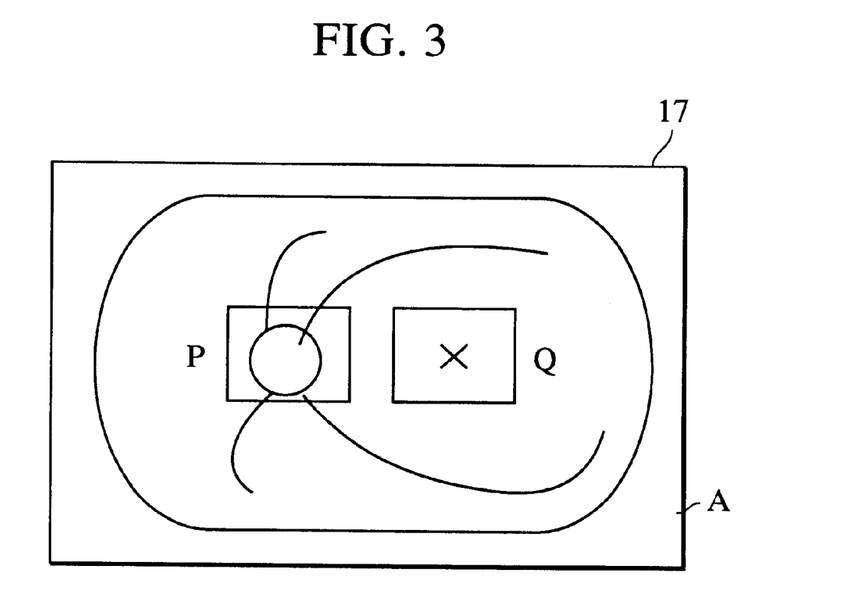
FIG. 3 is an illustration of an eyegrounds image.
Figure 4:
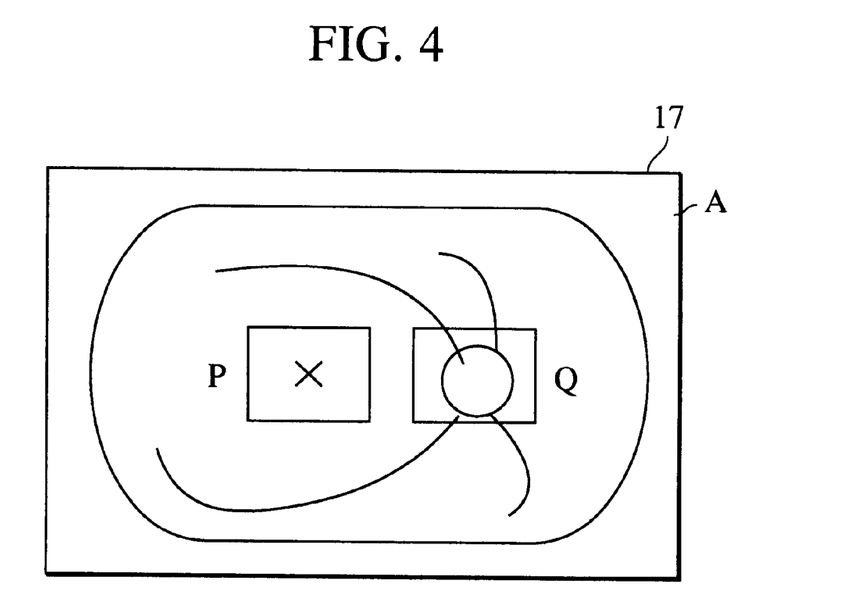
FIG. 4 is an illustration of an eyegrounds image.

FIGS. 3 and 4 show an eyegrounds image on an image-capturing device, which is obtained by presenting the fixed-viewing target 12 and by making the posterior pole portion of the eyegrounds Er the image center, with the target area setting section 19 being set to P and Q as target areas in advance. FIG. 3 shows an image when the left eye is photographed. FIG. 4 shows an image when the right eye is photographed. These images may be photographed in such a way that two light sources which differ for the right eye and the left eye are prepared and the operator prompts the examinee as to which fixed-viewing target 12 should be looked at, or in such a way that the operator selects right or left and the light source is switched according to this selection.

As shown in FIG. 3, the macula lutea (marked by x) is contained in an area Q, and a papilla (marked by o) is contained in an area P, and these areas P and Q are set as target areas. For these predetermined target areas (areas Q and P), the luminance level of the entirety or a part of sites within each area is detected. It is generally known that the luminance of the papilla is high and the luminance of the macula lutea is low. Therefore, when the luminance within the area P is greater than the luminance within the area Q, a determination that the examined eye is the left eye can be made, and the right-left eye detection switch can be omitted. Then, the highest luminance signal N is detected from among a plurality of pixel signals within the area P, and the lowest luminance signal M is detected from among a plurality of pixel signals within the area Q (steps 4 and 5).

When, in contrast, the eyegrounds of the examined eye is that of the right eye, since the macula lutea is in the area P and the papilla is in the area Q, in the area P, the lowest luminance signal M is detected from among a plurality of pixel signals, and in the area Q, the highest luminance signal N is detected from among a plurality of pixel signals.

Figure 5:
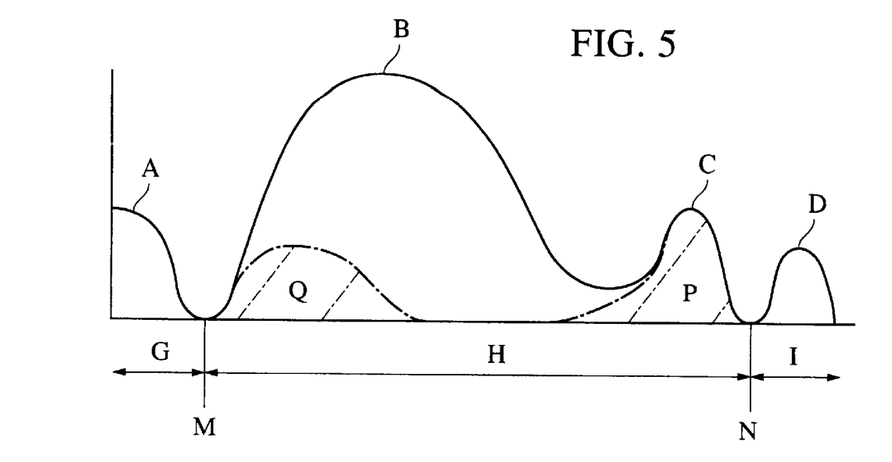
FIG. 5 is a graph of the histogram of an eyegrounds image.
Figure 6A:
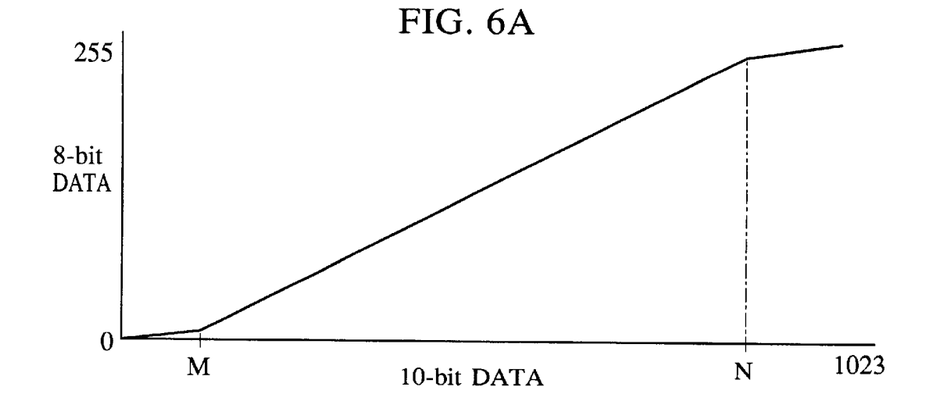
FIGS. 6A and 6B are graphs of a dynamic-range compression conversion table.

FIG. 5 shows the histogram of the luminance of the entire eyegrounds image (corresponding to the entirety of that captured by the image-capturing means 11); the horizontal axis indicates luminance, and the vertical axis indicates incidence. Each peak represents, from the side with lower luminance, an aperture portion A, a retina B, a papilla C, and a flare D which occurs due to a photographic error, etc. The area indicated by the single-dot chain line indicates luminance information detected from the area P and the area Q in the case of the left eye. In this manner, in this embodiment, the lowest luminance signal M and the highest luminance signal N are detected based on the digital data of only this area on the basis of the relationship in which the positions where the macula lutea and the papilla are present are determined in advance on the image-capturing plane without performing a detection operation for the entire image. A useful dynamic range H can be calculated (step 6) from the lowest luminance signal M and the highest luminance signal N. For example, dynamic-range compression, in which a compression ratio is set higher for areas G and I, and a compression ratio is set lower for an area H, is performed on 8-bit data (steps S7 and 8). Specifically, a conversion table such as that shown in FIG. 6A is prepared by the image processing section 15. M and N in FIG. 6 correspond to M and N in FIG. 4, respectively. After a compression process is performed using this conversion table, they are stored in the image memory 14 again (step S9).

More specifically, when the highest luminance signal N and the lowest luminance signal M in the areas P and Q are detected, a process is performed for setting the compression ratio to be low for the digital data which is present between the highest luminance signal N and the lowest luminance signal M from among the outputs of all the pixels of the image-capturing device, and a process is performed for setting the compression ratio to be high for the digital data which is not between the highest luminance signal N and the lowest luminance signal M. An image having fine gradations for the digital data of the eyegrounds image, primarily required for diagnosis, which is present between the highest luminance signal N and the lowest luminance signal M is obtained.

On the other hand, for the examiner, aperture and flare are unnecessary image information, and signal processing at coarse gradation is performed on these images.

Figure 6B:
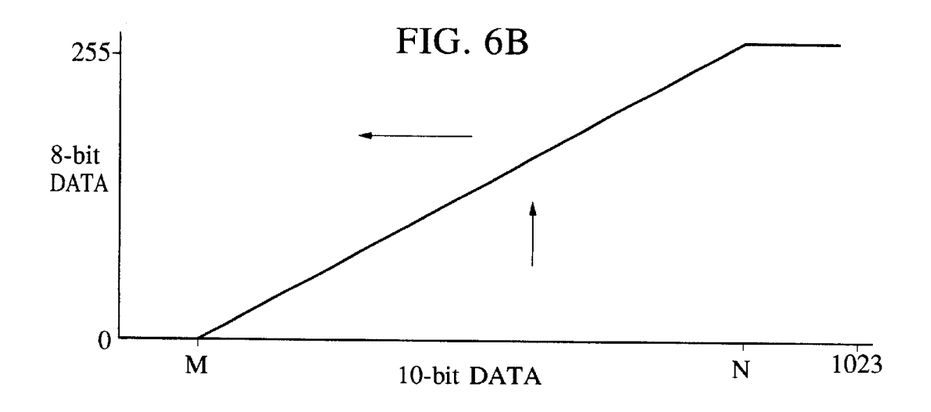

In this manner, it is possible to perform detection efficiently in a short time without checking all image information and it is possible to produce effective information with a small amount of data. In the dynamic-range compression method, the compression ratio is set high for the areas G and I. However, as shown in FIG. 6B, the information in the area G may be shifted to the lowest luminance value, and the information in the area I may be shifted to the highest luminance value in order to perform compression. Also, compression may not be performed on the information in the area H.

Although in this embodiment the lowest luminance value and the highest luminance value which are detected from the areas P and Q are defined as M and N, respectively, and are detected, detection is also possible in such a way that the area is divided into smaller portions and the average values of each site are compared. Alternatively, an area may be set to be small in advance so that M and N are determined from the average values of the entirety thereof. Also, for example, if M and N are detected from the average values of the several high-order or low-order pixels, or if particularly heterogeneous data is omitted, detection of stable M and N, which is not affected by noise components, becomes possible.

Although in this embodiment quantization is performed at a 10-bit resolution in the A/D conversion section 13 and conversion into 8-bit data is performed in the image processing section 15, input and output may be made at eight bits, a compression process may be performed for the areas G and I, and an expansion process may be performed on information in the area H. Furthermore, when a target area is set initially, the lowest luminance is detected from the area Q containing the macula lutea. However, when the luminance level of the peripheral portion of the image is lower due to an aberration in the optical system of the eyegrounds Er, that area may be set.

The eyegrounds image which is subjected to image processing in this manner is stored in the image memory 14. This image may be displayed on the monitor 17, may be printed out by a printer (not shown), may be stored in a portable recording medium, such as a magneto-optical disk (not shown), or may be transferred to an external apparatus by using a communication section.

Figure 7:
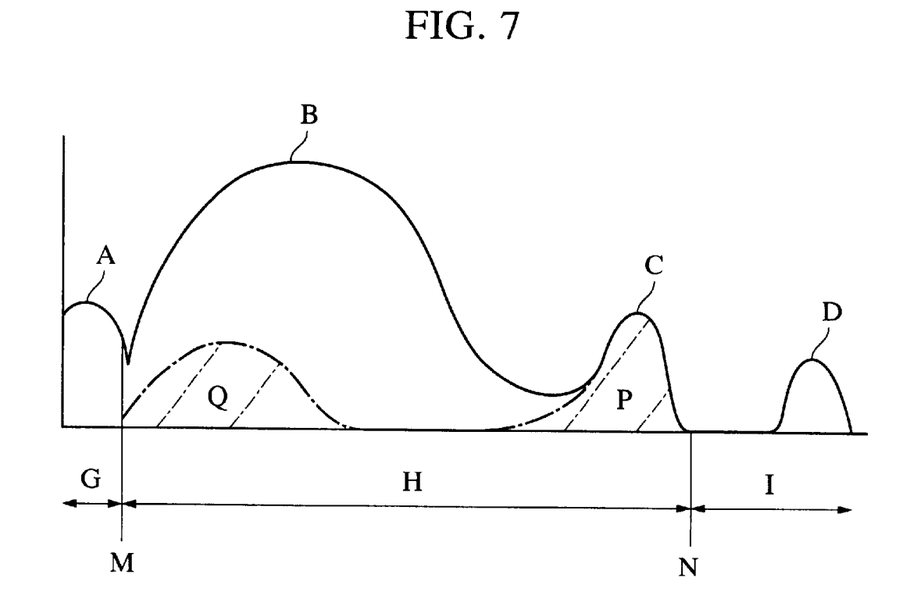
FIG. 7 is a graph of the histogram of an eyegrounds image.
Figure 8:
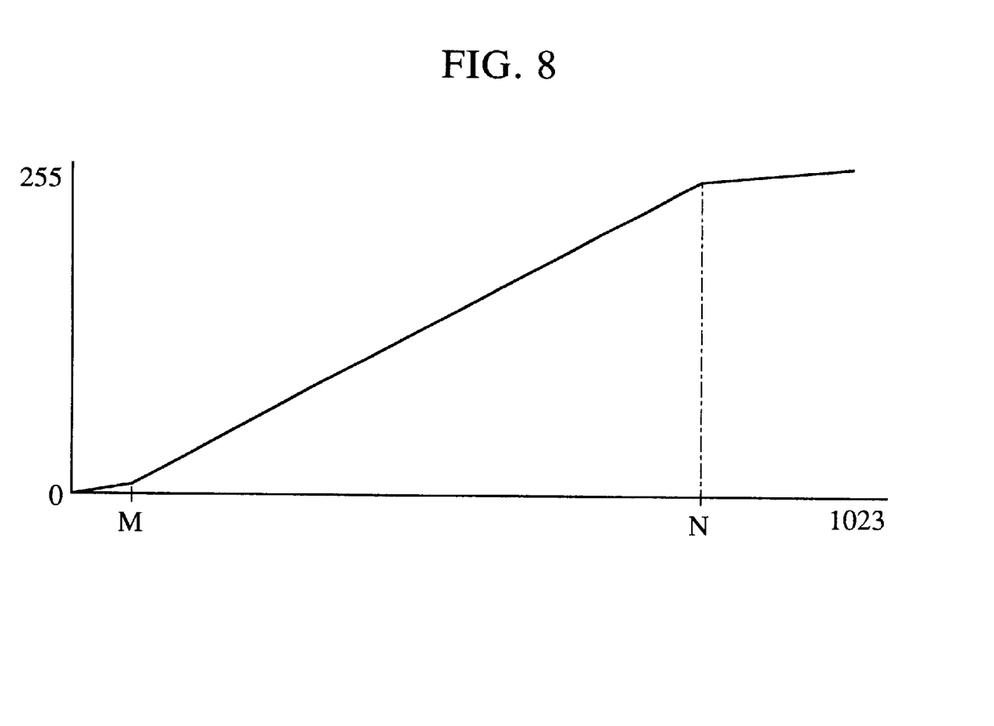
FIG. 8 is a graph of a dynamic-range compression conversion table.

FIG. 7 shows a histogram when an obtained image is too dark due to a setting error in the amount of photographic light or due to an individual difference in the eyegrounds Er. In a manner similar to that in FIG. 5, an aperture portion A, a retina portion B, a papilla C, a flare D which occurs due to a photographing error, etc., are shown from the side with lower luminance. Also in this case, the highest luminance signal N and the lowest luminance signal M in the areas P and Q are determined similarly. As shown in FIG. 8, by creating a conversion table for the range H from the lowest luminance signal M to the highest luminance signal N so that the compression ratio becomes lower, it is possible to efficiently produce an image without being influenced by setting errors in the amount of photographic light or by individual differences in the eyegrounds Er.

When, in contrast, an image which is too bright is obtained due to setting errors in the amount of photographic light or due to individual differences in the eyegrounds Er, it is possible to make a correction in a similar manner. Although the papilla and the macula lutea or peripheral portions thereof are set as a target area, target area changing means for setting a site to which the operator wishes to pay particular attention may be prepared so that the site is determined by making a calculation based on the output of the right-left eye detection means. For example, in a case in which the operator wishes to pay particular attention to the papilla, this can be achieved in such a way that, when the left eye is detected, the area P of FIG. 3 can be determined as the specially targeted site and the compression ratio of the peak of the papilla C of FIG. 5 is particularly set to be low.

Figure 9:
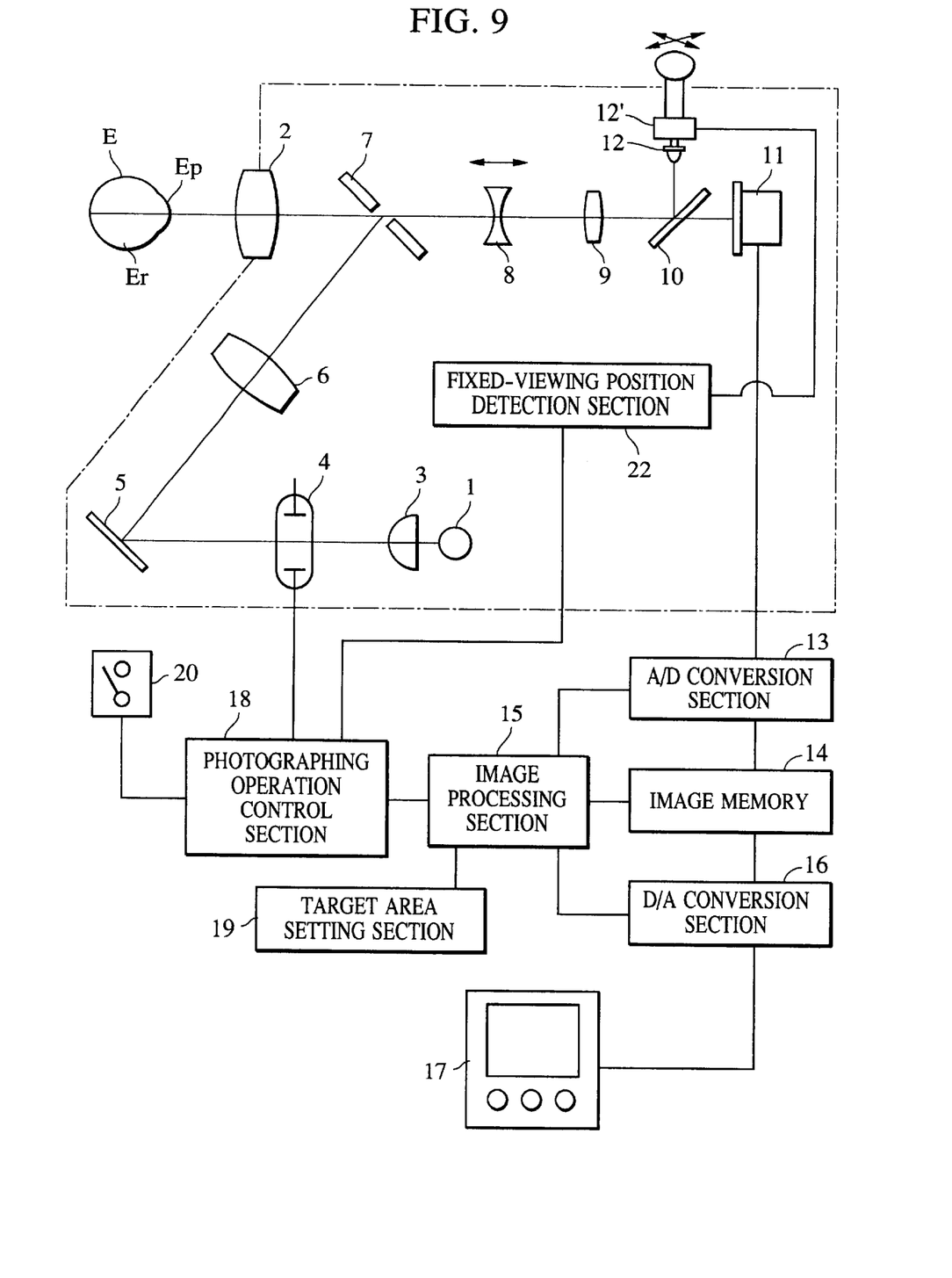
FIG. 9 shows the construction of a second embodiment of the present invention.

FIG. 9 shows the construction of a second embodiment of the present invention, in which, the fixed-viewing target 12 of the first embodiment is made movable and in which a fixed-viewing position detection section 22 has been added. The output of the fixed-viewing position detection section 22 is connected to the image processing section 15 and driving means 12' of the fixed-viewing target 12.

Figure 10:
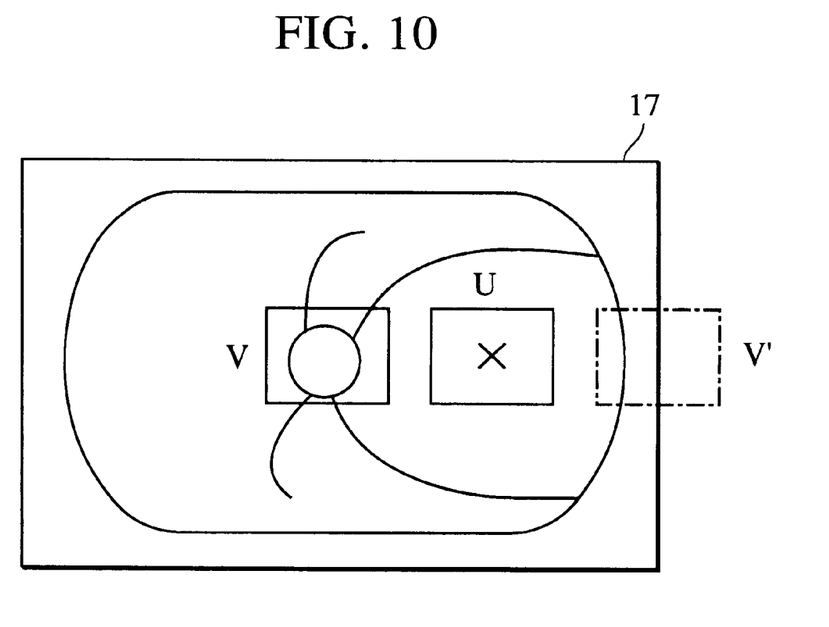
FIG. 10 Is an illustration of an eyegrounds image.

An examinee looks at the fixed-viewing target 12 in a manner similar to that in the first embodiment. Since the position of this fixed-viewing target 12 can be changed freely, an image in accordance with the fixed-viewing position, for example, as shown in FIG. 10, can be obtained. The image processing section 15, which detects that such an image is obtained, calculates, from the output of the fixed-viewing position detection section 22, that the macula lutea is positioned at nearly the center of an area U shown in FIG. 10 by taking into consideration the magnification of the optical system and the distance moved thereof. Based on the position of the macula lutea, it is expected that the papilla will be in an area V or V'. However, in this case, since the area V' is outside of the image area, the position of the papilla can be determined as being in the area V. Depending on the position of the fixed-viewing target 12, detection may be performed for both the areas V and V'. If the right-left eye detection means 21 is provided in a manner similar to that in the first embodiment, it is possible to determine the position of the papilla on the basis of both pieces of information.

Hereafter, in a manner similar to that in the first embodiment, the highest luminance and the lowest luminance are calculated from the set target area, a dynamic range is determined, and dynamic-range compression is performed. Also, in an apparatus capable of moving a fixed-viewing target freely, such a procedure makes it possible to produce effective information from a small amount of data by performing efficient detection in a short time without performing detection on the entire image information.

Although the papilla and the macula lutea are set as a target area, target area changing means for setting a site to which the operator wishes to pay particular attention may be prepared so that the site is determined by calculation from the output of the fixed-viewing position detection section 22.

Figure 11:
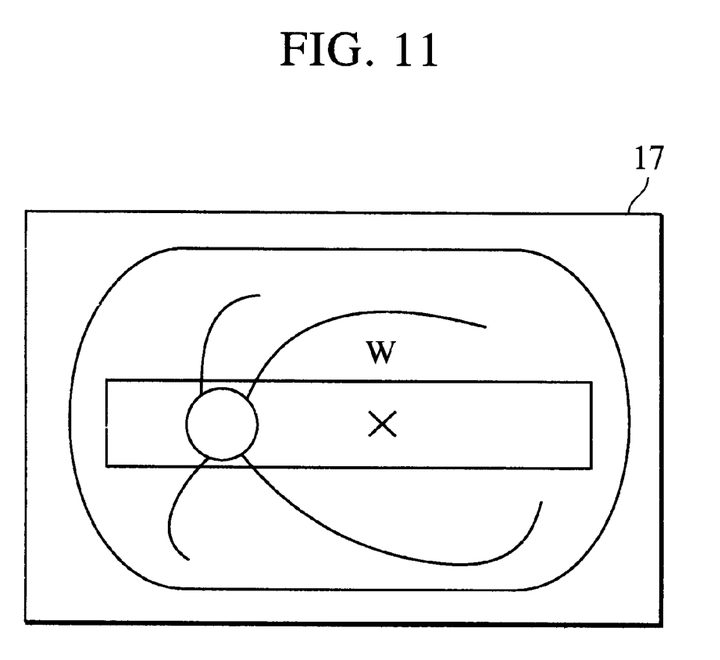
FIG. 11 is an illustration of an eyegrounds image.
Figure 12:
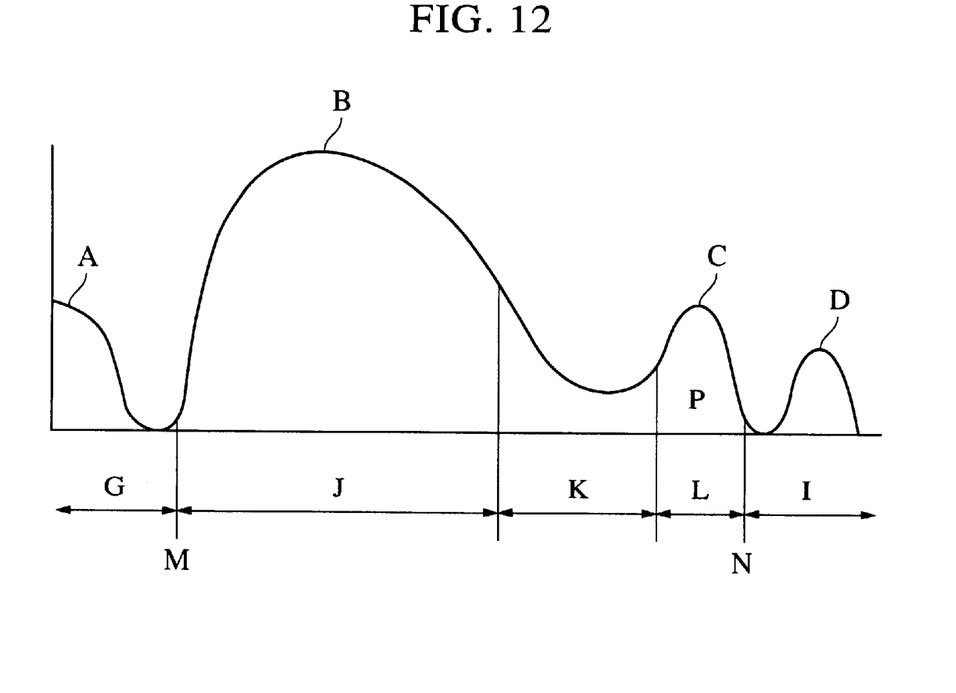
FIG. 12 is a graph of the histogram of an eyegrounds image.

FIG. 11 shows a target area according to a third embodiment of the present invention, also showing an example in which a target area W is set for a central narrow portion containing the macula lutea and the papilla of an obtained eyegrounds image. The image processing section 15 creates a histogram by determining the luminance information within the area W. FIG. 12 shows a histogram of the entire area. By performing detection within the area W, the rough shape of the peaks for the retina B and the papilla C can be extracted, and these peaks are divided into areas J, K, and L based on the preset reference value.

Figure 13:
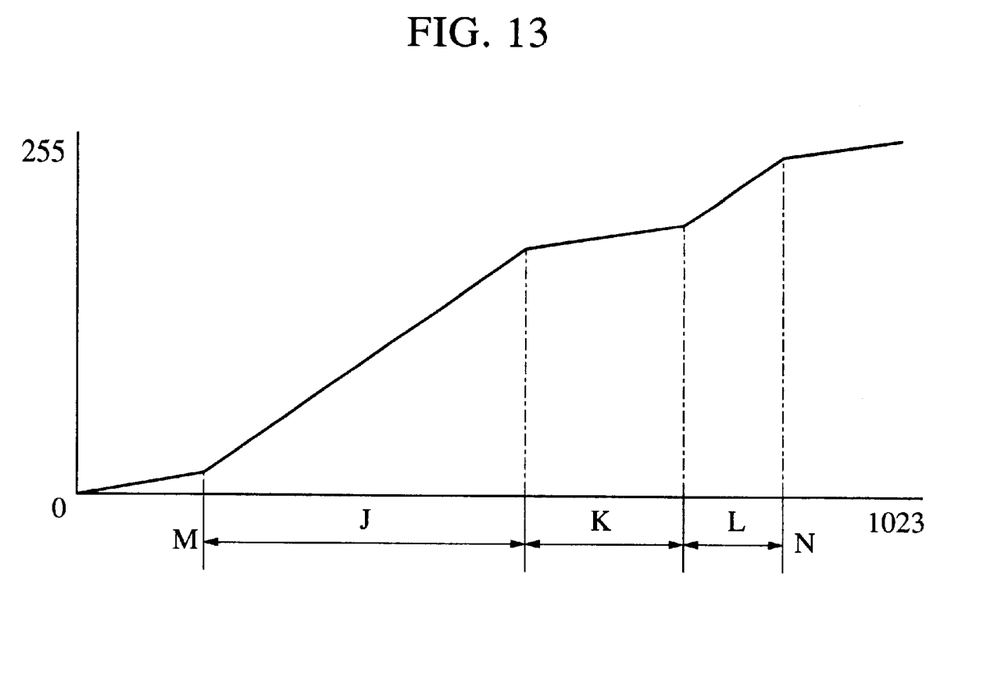
FIG. 13 is a graph of a dynamic-range compression conversion table.

FIG. 13 is a conversion table in which a compression ratio is set low with respect to the area J corresponding to the macula lutea and the area L corresponding to the papilla, containing large amounts of information. As described above, the information of the eyegrounds Er is divided into approximately three areas, a different compression ratio is set, and processing is performed on examined eye image information. As a result, a site to be specially targeted may be set in more detail, and necessary information can be created efficiently and effectively without being influenced by setting errors in the amount of photographic light or by individual differences in the eyegrounds Er.

As has thus been described, in the ophthalmogical photographing apparatus according to the present invention, the signal compression ratio of digital signals from an image-capturing device is set based on a high-level signal and a low-level signal in a predetermined area from among all the pixels. In particular, a compression ratio for a level signal which is present between a high-level signal and a low-level signal is set low, and a compression ratio for a level signal which is not present between a high-level signal and a low-level signal is set high. This makes it possible to obtain a high-gradation image for diagnostic purposes.

Many different embodiments of the present invention may be constructed without departing from the spirit and scope of the present invention. It should be understood that the present invention is not limited to the specific embodiments described in this specification. To the contrary, the present invention is intended to cover various modifications and equivalent arrangements included within the spirit and scope of the invention as hereafter claimed. The scope of the following claims is to be accorded the broadest interpretation so as to encompass all such modifications, equivalent structures and functions.

What is claimed is:

1. An ophthalmogical photographing apparatus comprising:
    an image-capturing device, having a plurality of pixels, for converting an image of an examined eye into electrical signals;
    a digital conversion section for converting the output of said plurality of pixels into digital signals;
    first and second detection means for detecting a high-level signal and a low-level signal, respectively, of a level signals indicating luminance levels of the digital signals in predetermined area pixels of said image-capturing device; and
    setting means for setting a signal compression ratio of the digital signals of said digital conversion section on the basis of the high-level signal and the low-level signal.

2. An ophthalmogical photographing apparatus according to claim 1, wherein said setting means sets the compression ratio of level signals by said digital conversion section that is present between the high-level signal and the low-level signal to differ from the compression ratio of level signals by said digital conversion section that is not present between the high-level signal and the low-level signal.

3. An ophthalmogical photographing apparatus according to claim 1, wherein said setting means sets the compression ratio of level signals by said digital conversion section that is present between the high-level signal and the low-level signal, to be smaller than the compression ratio of level signals by said digital conversion section that is not present between the high-level signal and the low-level signal.

4. An ophthalmogical photographing apparatus according to claim 1, wherein a predetermined pixel area for detecting the high-level signal contains the papilla of the examined eye, and a predetermined pixel area for detecting the low-level signal contains the macula lutea of the examined eye.

5. An ophthalmogical photographing apparatus according to claim 1, wherein a fixed-viewing target for guiding the fixed-viewing position of an examined eye is provided, and the predetermined pixel area is changed in accordance with the fixed-viewing target.

6. An ophthalmogical photographing apparatus according to claim 1, wherein the predetermined pixel area is a predetermined fixed area.

7. An ophthalmogical photographing apparatus comprising:
    image-capturing means for converting an examined eye image into electrical signals;
    a fixed-viewing target for directing the attention of the examined eye for fixed-viewing;
    area setting means for setting an image-capturing area of said image-capturing means in accordance with the position of the fixed-viewing target;
    luminance detection means for detecting the luminance of the examined eye image information obtained from said image-capturing means with respect to the area set by said area setting means; and
    image processing means for performing signal processing on image information of said image-capturing means in accordance with an output of said luminance detection means.

8. An ophthalmogical photographing apparatus according to claim 7, further comprising right-left eye determination means for determining whether the examined eye is the right eye or the left eye on the basis of the detection result of said luminance detection means.

9. An ophthalmogical photographing apparatus according to claim 7, wherein said image processing means comprises dynamic-range compression means for performing at least dynamic-range compression on a part of the examined eye image information.

10. An ophthalmogical photographing apparatus comprising:
- image-capturing means for converting an examined eye image into electrical signals;
- eye information generation means for generating information for indicating whether an examined eye is the right eye or the left eye;
- luminance detection means for detecting luminance information with respect to a predetermined area of said image-capturing means in accordance with an output of said eye information generation means; and
- image processing means for performing signal processing on examined eye image information by said image-capturing means in accordance with an output of said luminance detection means.

11. An ophthalmogical photographing apparatus according to claim 10, where said image processing means comprises dynamic-range compression means for performing at least dynamic-range compression on a part of the examined eye image information.

12. An ophthalmogical photographing apparatus comprising:
- an image-capturing device which captures an image of an eye to be examined so as to obtain digital image data; and
- a processor which performs data compression to the image data obtained by said image-capturing device based on luminance information relating to a limited target area in the image of the eye to be examined.

13. An apparatus according to claim 12, wherein said processor serves to set a relatively low compression ratio to pixels of the image data within a luminance range relating to the limited target area, and to set a relatively high compression ratio to pixels outside the luminance range.

14. An apparatus according to claim 13, wherein the limited target area contains at least one of papilla of the eye and macula lutea of the eye.

15. An apparatus according to claim 13, wherein said processor detects a high-luminance pixel and a low-luminance pixel of the image data within the limited target area to determine the luminance range.

16. An apparatus according to claim 13, wherein said processor performs dynamic-range compression.

17. An apparatus according to claim 16, wherein said processor performs dynamic-range compression using a conversion table.

18. An apparatus according to claim 12, wherein the limited target area contains at least one of papilla of the eye and macula lutea of the eye.

19. An apparatus according to claim 12, further comprising an image memory which stores the image data obtained by said image-capturing device.

20. An apparatus according to claim 19, wherein said image memory stores uncompressed image data obtained by said image-capturing device, then stores compressed image data compressed by said processor.

21. An apparatus according to claim 12, wherein said processor also serves to determine whether the examined eye is a right eye or a left eye on the basis of the luminance information.

22. An apparatus according to claim 12, further comprising a movable fixed-viewing target for guiding the eye to be examined, and the limited target area is set in accordance with a position of the fixed-viewing target.

23. An ophthalmogical photographing method comprising:
- capturing, with an image-capturing device, an image of an eye to be examined so as to obtain digital image data; and
- performing data compression to the image data obtained by the image-capturing device based on pixels of the digital image data relating to a limited target area in the image of the eye to be examined.

24. A method according to claim 23, further comprising a step of setting the limited target area which contains at least one of papilla of the eye and macula lutea of the eye.

25. A method according to claim 24, wherein said setting step comprises detecting a high-luminance pixel and a low-luminance pixel of the image data within the limited target area to set compression ratio.

26. A method according to claim 25, wherein said compression ratio comprises a relatively low compression ratio being applied to pixels within a luminance range between the low-luminance pixel and the high-luminance pixel, and a relatively high compression ratio being applied to pixels outside the luminance range.

27. A method according to claim 23, further comprising moving a fixed-viewing target to guide the eye to be examined, and the limited target area is set in accordance with a position of the fixed-viewing target.

* * * * *

UNITED STATES PATENT AND TRADEMARK OFFICE
CERTIFICATE OF CORRECTION

PATENT NO.   : 6,244,710 B1
DATED        : June 12, 2001
INVENTOR(S)  : Tetsuji Ogawa Page 1 of 1

It is certified that error appears in the above-identified patent and that said Letters Patent is hereby corrected as shown below:

Title page,
Item [54], "OPHTHALMOGICAL" should read -- OPHTHALMOLOGICAL --.
Item [57], ABSTRACT, line 5, "ophthalmogical" should read -- ophthalmological --.

Column 1,
Lines 7, 11, 44, 52 and 58, "ophthalmogical" should read -- ophthalmological --;

Column 2,
Lines 25 and 39, "ophthalmogical" should read -- ophthalmological --.

Column 3,
Line 7, "Is" should read -- is --; and
Line 59, "mirror 7" should read -- mirror 7, --.

Column 7,
Line 50, "ophthalmogical" should read -- ophthalmological --.

Column 8,
Lines 7, 22, 29, 36, 41, 46, 49 and 66, "ophtalmogical" should read
-- ophthalmological --.
Line 15, "a level signal" should read -- level signals --;

Column 9,
Lines 4, 9, 24 and 29, "ophthalmogical" should read -- ophthalmological --.

Column 10,
Line 24, "ophthalmogical" should read -- ophthalmological --.

Signed and Sealed this

Twenty-first Day of May, 2002

*Attest:*

*Attesting Officer*

JAMES E. ROGAN
*Director of the United States Patent and Trademark Office*